(12) United States Patent
Schmitt et al.

(10) Patent No.: US 7,750,179 B2
(45) Date of Patent: Jul. 6, 2010

(54) METHOD OF PURIFYING (METH) ACRYLATES

(75) Inventors: Bardo Schmitt, Mainz (DE); Joachim Knebel, Alsbach-Haehnlein (DE); Guenther Graeff, Alsbach-Haehnlein (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 12/093,744

(22) PCT Filed: Oct. 11, 2006

(86) PCT No.: PCT/EP2006/067293

§ 371 (c)(1), (2), (4) Date: May 15, 2008

(87) PCT Pub. No.: WO2007/087903

PCT Pub. Date: Aug. 9, 2007

(65) Prior Publication Data

US 2008/0300373 A1    Dec. 4, 2008

(30) Foreign Application Priority Data

Jan. 12, 2006    (DE) ..................... 10 2006 007 771

(51) Int. Cl.
   *C07C 67/48*    (2006.01)
(52) U.S. Cl. ..................................... 560/218
(58) Field of Classification Search ........... None
   See application file for complete search history.

(56) References Cited

U.S. PATENT DOCUMENTS

| | | | |
|---|---|---|---|
| 6,080,794 A | 6/2000 | Auschra et al. | |
| 6,409,778 B1 | 6/2002 | Auschra et al. | |
| 6,458,750 B1 | 10/2002 | Dardin et al. | |
| 6,639,099 B1 | 10/2003 | Knebel et al. | |
| 7,429,555 B2 | 9/2008 | Scherer et al. | |
| 7,452,932 B2 | 11/2008 | Scherer et al. | |
| 2006/0142168 A1 | 6/2006 | Kinker et al. | |
| 2006/0189490 A1 | 8/2006 | Dardin et al. | |
| 2007/0191238 A1 | 8/2007 | Fischer et al. | |
| 2007/0213237 A1 | 9/2007 | Scherer et al. | |
| 2008/0132663 A1 | 6/2008 | Acker et al. | |

FOREIGN PATENT DOCUMENTS

| | | |
|---|---|---|
| DE | 101 27 941 | 5/2002 |
| DE | 10 2004 014 684 | 10/2005 |
| EP | 0 736 510 | 10/1996 |
| JP | 411228523 | * 8/1999 |

OTHER PUBLICATIONS

Database CAS online citation for JP 01042463, citation No. 1989:553220 [retrieved Feb. 10, 2010] from STN; Columbus, OH, USA.*
Machine Translation for JP 411228523.*
U.S. Appl. No. 12/306,019, filed Dec. 22, 2008, Boehmke, et al.
U.S. Appl. No. 11/995,406, filed Jan. 11, 2008, Schmitt, et al.
U.S. Appl. No. 12/088,093, filed Mar. 26, 2008, Schmitt, et al.
U.S. Appl. No. 12/092,507, filed May 2, 2008, Klesse, et al.
U.S. Appl. No. 61/014,927, filed Dec. 12, 2007, Karnbrock.
U.S. Appl. No. 12/159,871, filed Jul. 2, 2008, Wiesler, et al.

* cited by examiner

*Primary Examiner*—Karl J Puttlitz
(74) *Attorney, Agent, or Firm*—Oblon, Spivak, McClelland, Maier & Neustadt, L.L.P.

(57) ABSTRACT

The invention relates to a process for purifying (meth)acrylates.

27 Claims, No Drawings

METHOD OF PURIFYING (METH) ACRYLATES

The invention relates to a process for reducing the alcohol content in (meth)acrylates and to their uses.

(Meth)acrylates have a wide variety of fields of use. (Meth) acrylates are monomers which can be converted in polymerization reactions, for example to polymethacrylates. (Meth) acrylate polymers can also be used as binders or additives in paints, varnishes, coatings, etc. (Meth)acrylates are also utilized in the form of their polymers in the pharmaceutical industry, for example to coat tablets. A high purity is usually very advantageous.

In the literature, various ways can be found of purifying (meth)acrylates. In addition to distillation, treatment with adsorbents and extraction with solvents are described.

JP 2003261509 describes a transesterification in the presence of Sn catalysts. To remove the catalyst, the reaction mixture is treated with acidic ion exchange resin.

JP 01052747 describes the preparation of isocyanate-containing methacrylates. They are purified by distilling and Cl-containing impurities are removed by working with a molecular sieve (NaA zeolite). However, this process can only remove hydrolysable compounds.

JP 2003048866 describes a transesterification in the presence of titanates and treatment with alumina to remove the catalyst.

It was an object of the invention to prepare (meth)acrylates in high purity and with high yields.

The object was achieved by a process for working-up (meth)acrylates, characterized in that an isocyanate/catalyst mixture is added and then the mixture is distilled.

It has been found that the resulting product comprises only small amounts of alcohol. It has not been possible with conventional purification processes to prepare residual alcohol contents below 0.1% by weight. For many sensitive reactions, for example anionic polymerizations, this is too high a residual alcohol content. The process according to the invention can achieve residual alcohol contents of <0.01% by weight.

It has been found that, surprisingly, the work-up proceeds stably. No polymers are found as an impurity, since there was a risk of a side reaction of the isocyanates with the phenolic stabilizers.

It has been found that the purities can be increased, depending on the reactant, in some cases 99.9%.

An isocyanate/catalyst mixture is used.

The isocyanates used may be all mono- or polyfunctional isocyanates. Preference is given to all common diisocyanates such as toluene diisocyanate, hexane diisocyanate, isophorone diisocyanate, 2,2,4-trimethyl-hexamethylene diisocyanate, diphenylmethane diisocyanate, dicyclohexylmethane diisocyanate.

The catalysts used may be all known isocyanate activators. Preference is given to using amines, particular preference to using diazabicyclooctane. However, preference is also given to using organotin compounds, more preferably dioctyltin oxide, tin dilaurate or tin diethylhexanoate.

The isocyanate/catalyst mixture is composed of the calculated amounts of isocyanate and 0.01 to 1% catalyst, based on the monomer weighed in.

The isocyanate is added in equimolar amounts, but preferably in excess, relative to the concentration of impurities such as water and/or alcohol.

The quantitative ratio is 1:1 to 10:1, more preferably 1:1 for diisocyanates (isocyanate:impurity).

The purification is effected in two steps. First, the (meth) acrylates are stirred at 60 to 90° C., preferably at 80° C., for 1 to 6 hours after the addition of isocyanates.

Subsequently, the (meth)acrylates are distilled. Depending on the (meth)acrylate, the distillation is effected at standard pressure or under reduced pressure. The distillation is preferably carried out at conditions of 60 to 140° C. and 0.1 to 10 mbar.

The notation (meth)acrylate here means both methacrylate, for example methyl methacrylate, ethyl methacrylate, etc., and acrylate, for example methyl acrylate, ethyl acrylate, etc., and mixtures of the two.

The particularly low residual alcohol content enables many fields of use of the (meth)acrylates purified by the present process. These (meth)acrylates may preferably be used in anionic polymerizations, group transfer polymerization (GTP), ATRP, RAFT and all polymerization techniques which are sensitive towards impurities.

The examples given below are given for better illustration of the present invention, but are not capable of restricting the invention to the features disclosed herein.

EXAMPLES

Comparative Example 1

CE 1

1600.0 g of ethylhexyl methacrylate, containing 0.040 mol of water and 0.160 mol of ethylhexanol The mixture is weighed in. The monomers are admixed with 50-100 ppm of HQME (hydroquinone monomethyl ether). The product is distilled using a column. After first runnings, the main fraction is obtained as methacrylate/product.

Comparative Example 2

CE 2

1600.0 g of ethylhexyl methacrylate, containing 0.070 mol of water and 0.130 mol of ethylhexanol 78.9 g=0.47 mol of hexamethylene diisocyanate The mixture is weighed in without catalyst and the isocyanate is added in a molar excess, compared with the sum of residual alcohol and water content. The monomers are admixed with 50-100 ppm of HQME (hydroquinone monomethyl ether). After stirring at approx. 80° C. for three hours, the product is distilled through a column. After first runnings, the main fraction is obtained as methacrylate/product with reduced alcohol content.

Example 3

E 3

1580.0 g of ethylhexyl methacrylate, containing 0.040 mol of water and 0.160 mol of ethylhexanol 33.6 g=0.2 mol of hexamethylene diisocyanate 1.6 g of tin(II) ethylhexanoate (0.1% based on ethylhexyl methacrylate)

The mixture is weighed in and the isocyanate is added in a molar excess, compared with the sum of residual alcohol and water content. The monomers are admixed with 50-100 ppm of HQME (hydroquinone monomethyl ether). After stirring at approx. 80° C. for three hours, the product is distilled through a column. After first runnings, the main fraction is obtained as methacrylate/product with minimized alcohol content.

Example 4

E 4

1600.0 g of butyldiglycol methacrylate, containing 0.070 mol of water and 0.045 mol of butyldiglycol
19.3 g=0.115 mol of hexamethylene diisocyanate
1.6 g of tin(II) ethylhexanoate (0.1% based on butyldiglycol methacrylate)

The mixture is weighed in and the isocyanate is added in a molar excess, compared with the sum of residual alcohol and water content. The monomers are admixed with 50-100 ppm of HQME (hydroquinone monomethyl ether). After stirring at approx. 80° C. for three hours, the product is distilled through a column. After first runnings, the main fraction is obtained as methacrylate/product with minimized alcohol content.

All further experiments are calculated analogously.

Mixture Calculation:

| Exp. No.: | Reactants | Residual alcohol [mmol] | Water [mmol] | Isocyanate [mmol] |
|---|---|---|---|---|
| CE 1 | Ethylhexyl methacrylate | 160 | 40 | 0 |
| CE 2 | Ethylhexyl methacrylate | 130 | 70 | 470 |
| E 3 | Ethylhexyl methacrylate | 160 | 40 | 200 |
| E 4 | Butyldiglycol methacrylate | 45 | 70 | 115 |
| E 5 | Benzyl methacrylate | 160 | 150 | 310 |
| E 6 | Ethyltriglycol methacrylate | 210 | 80 | 290 |
| E 7 | Methyltriglycol methacrylate | 315 | 60 | 375 |

Analysis:

| Example | Monomer | Residual alcohol [% by wt.] | Water [ppm] | Purity [% by wt.] |
|---|---|---|---|---|
| CE 1 reactant | Ethylhexyl methacrylate | 0.13 | 60 | 99.3 |
| CE 1 product | Ethylhexyl methacrylate | 0.13 | 60 | 99.6 |
| CE 2 reactant | Ethylhexyl methacrylate | 0.10 | 70 | 99.5 |
| CE 2 product | Ethylhexyl methacrylate | 0.10 | 60 | 99.6 |
| E 3 reactant | Ethylhexyl methacrylate | 0.13 | 40 | 99.0 |
| E 3 product | Ethylhexyl methacrylate | <0.01 | 40 | 99.9 |
| E 4 reactant | Butyldiglycol methacrylate | 0.46 | 790 | 97.7 |
| E 4 product | Butyldiglycol methacrylate | <0.01 | <10 | 99.2 |
| E 5 reactant | Benzyl methacrylate | 0.14 | 170 | 99.2 |
| E 5 product | Benzyl methacrylate | <0.01 | <10 | 99.7 |
| E 6 reactant | Ethyltriglycol methacrylate | 0.23 | 100 | 94.2 |
| E 6 product | Ethyltriglycol methacrylate | 0.04 | 100 | 97.4 |
| E 7 reactant | Methyltriglycol methacrylate | 0.36 | 100 | 97.9 |
| E 7 product | Methyltriglycol methacrylate | 0.03 | 100 | 99.1 |

Comparative Example 1 shows that a normal column distillation does not lead to improved product quality with regard to the residual alcohol content.

Comparative Example 2 shows that treatment of the starting material with isocyanate without the customary isocyanate catalyst with subsequent column distillation likewise does not lead to any product improvement.

Examples 3 to 7 show that the inventive work-up of the (meth)acrylates leads to a minimization of the residual alcohol content and hence to an optimization of the product quality.

The invention claimed is:

1. A process for purifying a (meth)acrylate, comprising:
   combining the (meth)acrylate with a mono- or polyfunctional isocyanate and a catalyst selected from the group consisting of diazabicyclooctane and organotin compounds to provide a mixture; and
   distilling the (meth)acrylate from the mixture.

2. The process according to claim 1, wherein the catalyst is selected from the group consisting of dioctyltin oxide, tin dilaurate and tin diethylhexanoate.

3. The process according to claim 1, wherein the catalyst is diazabicyclooctane.

4. The process according to claim 1, wherein the isocyanate is added in an equimolar ratio or in excess relative to a concentration of an impurity in the (meth)acrylate that is reactive with the isocyanate.

5. The process according to claim 4, wherein the isocyanate:impurity ratio is from 1:1 to 10:1.

6. The process according to claim 4, wherein the impurity is water, alcohol or both.

7. The process according to claim 1, wherein the mono- or polyfunctional isocyanate is selected from the group consisting of toluene diisocyanate, hexane diisocyanate, isophorone diisocyanate, 2,2,4-trimethylhexamethylene diisocyanate, diphenylmethane diisocyanate and dicyclohexylmethane diisocyanate.

8. The process according to claim 1, wherein the catalyst is present in an amount of from 0.01 to 1% by weight, based on amount of (meth)acrylate.

9. The process according to claim 1, wherein the (meth)acrylate is combined with the mono- or polyfunctional isocyanate and catalyst, and the Resulting mixture stirred for 1 to 6 hours at a temperature of from 60 to 90° C., followed by Distillation of the (meth)acrylate at standard pressure or reduced pressure.

10. The process according to claim 1, wherein the (meth)acrylate is a member selected from the group consisting of methyl methacrylate, ethyl methacrylate, methyl acrylate, ethyl acrylate, ethylhexyl methacrylate, butyldiglycol methacrylate, benzyl methacrylate, methyltriglycol methacrylate and mixtures thereof.

11. A process for purifying a (meth)acrylate, comprising:
combining the (meth)acrylate with a diisocyanate and a catalyst selected from the group consisting of amines and organotin compounds to provide a mixture; and
distilling the (meth)acrylate from the mixture;
wherein the diisocyanate is a member selected from the group consisting of toluene diisocyanate, hexane diisocyanate, isophorone diisocyanate, 2,2,4-trimethylhexamethylene diisocyanate, disphenylmethane diisocyanate and dicyclohexylmethane diisocyanate.

12. The process according to claim 11, wherein the catalyst is selected from the group consisting of dioctyltin oxide, tin dilaurate and tin diethylhexanoate.

13. The process according to claim 11, wherein the catalyst is diazabicyclooctane.

14. The process according to claim 11, wherein the isocyanate is added in an equimolar ratio or in excess relative to a concentration of an impurity in the (meth)acrylate That is reactive with the isocyanate.

15. The process according to claim 14, wherein the isocyanate:impurity ratio is from 1:1 to 10:1.

16. The process according to claim 14, wherein the impurity is water, alcohol or both.

17. The process according to claim 11, wherein the catalyst is present in an amount of from 0.01 to 1% by weight, based on amount of (meth)acrylate.

18. The process according to claim 11, wherein the (meth)acrylate is combined with the mono- or polyfunctional isocyanate and catalyst, and the resulting mixture Stirred for 1 to 6 hours at a temperature of from 60 to 90° C., followed by distillation of the (meth)acrylate at standard pressure or reduced pressure.

19. The process according to claim 11, wherein the (meth)acrylate is a member selected from the group consisting of methyl methacrylate, ethyl methacrylate, methyl acrylate, ethyl acrylate, ethylhexyl methacrylate, butyldiglycol methacrylate, benzyl methacrylate, methyltriglycol methacrylate and mixtures thereof.

20. A process for purifying a (meth)acrylate, comprising:
combining the (meth)acrylate with a mono- or polyfunctional isocyanate and a catalyst selected from the group consisting of amines and organotin compounds to provide a mixture; and
distilling the (meth)acrylate from the mixture;
wherein the (meth)acrylate is a member selected from the group consisting of methyl methacrylate, ethyl methacrylate, methyl acrylate, ethyl acrylate, ethylhexyl methacrylate, butyldiglycol methacrylate, benzyl methacrylate, methyltriglycol methacrylate and mixtures thereof.

21. The process according to claim 20, wherein the catalyst is selected from the group consisting of dioctyltin oxide, tin dilaurate and tin diethylhexanoate.

22. The process according to claim 20, wherein the catalyst is diazabicyclooctane.

23. The process according to claim 20, wherein the isocyanate is added in an equimolar ratio or in excess relative to a concentration of an impurity in the (meth)acrylate that is reactive with the isocyanate.

24. The process according to claim 23, wherein the isocyanate:impurity ratio is from 1:1 to 10:1.

25. The process according to claim 23, wherein the impurity is water, alcohol or both.

26. The process according to claim 20, wherein the catalyst is present in an amount of from 0.01 to 1% by weight, based on amount of (meth)acrylate.

27. The process according to claim 20, wherein the (meth)acrylate is combined with the mono- or polyfunctional isocyanate and catalyst, and the resulting mixture stirred for 1 to 6 hours at a temperature of from 60 to 90° C., followed by distillation of the (meth)acrylate at standard pressure or reduced pressure.

* * * * *

UNITED STATES PATENT AND TRADEMARK OFFICE
CERTIFICATE OF CORRECTION

| | | |
|---|---|---|
| PATENT NO. | : 7,750,179 B2 | Page 1 of 1 |
| APPLICATION NO. | : 12/093744 | |
| DATED | : July 6, 2010 | |
| INVENTOR(S) | : Schmitt et al. | |

It is certified that error appears in the above-identified patent and that said Letters Patent is hereby corrected as shown below:

On the title page, Item (30), the Foreign Application Priority Data is incorrect. Item (30) should read:

-- (30)      Foreign Application Priority Data

Jan. 12, 2006    (DE) ................................ 10 2006 001 771 --

Signed and Sealed this

Twelfth Day of October, 2010

David J. Kappos
*Director of the United States Patent and Trademark Office*